United States Patent [19]
Ollat et al.

[11] Patent Number: 5,863,925
[45] Date of Patent: Jan. 26, 1999

[54] USE OF SULBUTIAMINE IN THE TREATMENT OF PARKINSON'S DISEASE, SCHIZOPHRENIA, ALCOHOLISM, AND DYSTHYMIA

[75] Inventors: Hélène Ollat, Nesle la Gilberde; Alain Le Ridant, Neuilly sur Seine; Laurent Perret, Paris, all of France

[73] Assignee: Adir et Compagnie, Courbevoie, France

[21] Appl. No.: 943,564

[22] Filed: Oct. 3, 1997

[30] Foreign Application Priority Data

Oct. 4, 1996 [FR] France .................................. 96 12112

[51] Int. Cl.⁶ ..................................................... A61K 31/51
[52] U.S. Cl. .............................................................. 514/276
[58] Field of Search ................................................ 514/276

[56] References Cited

PUBLICATIONS

Micheau et al, Biological Abstracts, vol. 81, abstract No. 7352, 1985.
Servier, Chemical Abstracts, vol. 88, abstract No. 158486, 1978.
Science Union et al, Chemical Abstracts, vol. 89, abstract No. 100361, 1978.

*Primary Examiner*—William R. A. Jarvis
*Attorney, Agent, or Firm*—The Firm of Gordon W. Hueschen

[57] ABSTRACT

The invention relates to the use of sulbutiamine and pharmaceutical compositions thereof for the treatment of Parkinson's Disease, Schizophrenia, alcoholism, and dysthymia.

2 Claims, No Drawings

USE OF SULBUTIAMINE IN THE TREATMENT OF PARKINSON'S DISEASE, SCHIZOPHRENIA, ALCOHOLISM, AND DYSTHYMIA

BACKGROUND OF THE INVENTION

The present invention relates to the use of sulbutiamine and pharmaceutical compositions thereof for the treatment of certain psychomotor and psychointellectual disorders, characterized by the delay, the slowing and the depression of behavioral and intellectual responses demanding the strategic mobilization of percepts and mental concepts. These disorders are observed in particular in Parkinson's patients, deficient schizophrenics, alcoholics, major depressives and dysthymics.

PRIOR ART DESCRIPTION

Sulbutiamine is an active principle which is already known and described in the literature. The special medicament patent 5921 M has described this product as an agent having the activity of vitamin $B_1$, capable of causing a raised vitamin $B_1$ blood level and able to exert effects with respect to all the symptoms of $B_1$ avitaminosis.

The special medicament patent 5921 M likewise mentions that for these therapeutic ends, the product is used in the form of tablets containing 5 to 50 mg of product per unit dose.

Finally, Belgian Patent BE 845,260 describes the pyschoanaleptic properties of sulbutiamine, which allow neurodepressant effects of sedatives or of neuroleptics to be antagonized.

For its part, Vidal recommends the use of sulbutiamine for the treatment of certain physical or psychological inhibition states with decline in activity and apathy.

DESCRIPTION OF THE INVENTION

The Applicant has now demonstrated that the administration of sulbutiamine allows recovery from psychomotor and psycho-intellectual disorders described in the first paragraph, in Parkinson's patients, deficient schizophrenics, alcoholics hospitalized for subsequent cure of alcohol deprival, dysthymic patients or alternatively patients suffering major depressive episodes.

In the different studies conducted on these patients, sulbutiamine has in every case allowed psychomotor slowing, inhibition of action, intellectual strategy disorders as well as executive function disorders to be avoided.

The pharmaceutical compositions used according to the invention contain sulbutiamine, alone or in combination with one or more inert, nontoxic, pharmaceutically acceptable vehicles.

The medicaments intended for the treatment of psychomotor and intellectual disorders in these subjects, obtained using sulbutiamine according to the invention, will be present in the form of pharmaceuticals suitable for administration by the oral, parenteral, transcutaneous, nasal, rectal or perlingual route, especially tablets, sublingual tablets, glossettes, gelatin capsules, capsules, tablets, suppositories, transdermal patches, buccal patches, etc . . .

The dosage varies according to the age and the weight of the patient, the administration route, the nature of the therapeutic indication and of the associated treatments, and ranges from 400 mg to 800 mg per day orally.

CLINICAL STUDIES

EXAMPLE 1

Effects of Sulbutiamine on the Psycho-Cognitive Evolution of Alcohol-Dependent and Deprived Patients The study was carried out on a population of hospitalized alcohol-dependent patients after a deprival cure.

These patients were divided into two parallel groups and were treated under double-blind conditions for 6 weeks, either with sulbutiamine, or with a placebo, the treatments being allocated according to a randomization code.

We evaluated, with the aid of the following tests, the effects of the treatment on:

1 - cognitive and executive functions and attention:
   cognitive potential evoked,
   Stroop test,
   trail making test
   MADRS scale (concentration difficulties).
2 - mnesic functions:
   Benton test,
   Rey figure,
   Wechsler scale.
3 - mood and anxiety:
   MADRS scale (emotional dulling, decline in activity),
   HARS scale (withdrawal),
   Beck scale (decline in activity).

In these alcohol-dependent and deprived patients, treated with sulbutiamine, an improvement of the cognitive and mnesic functions and the attention was observed.

EXAMPLE 2

Effects of Sulbutiamine on Cognitive Slowing, Objective and Subjective, and on the Feeling of Fatigue of Parkinson's Patients The study was carried out on a population of patients having idiopathic Parkinson's disease, treated by L-dopa and/or dopaminergic agonists, stable on entry into the study, without major fluctuations of the motor state and without signs of dementia.

These patients were divided into 2 parallel groups and were treated under double-blind conditions for 8 weeks, either with sulbutiamine, or with a placebo, the treatments being allocated according to a randomization code.

By means of the following tests, we evaluated the effects of the treatment on:

1 - the cognitive functions, attention, verbal, ideational and motor slowing:
   test of 15 objects,
   Stroop test,
   MADRS scale (concentration difficulties),
   verbal fluency test,
   trail making test.
2 - the executive functions:
   odd man out test,
   Wais-R.
3 - mnesic functions:
   Gröber and Buschke test.
4 - sensation of fatigue:
   self-evaluation of fatigue.
5 - mood:
   MADRS scale (emotional dulling, decline in activity).

In Parkinson's patients, treated with sulbutiamine, an improvement in the cognitive, executive and mnesic functions was observed, with diminution of the sensation of fatigue.

EXAMPLE 3
Effects of Sulbutiamine on the Inhibition Symptoms in Dysthymic Patients The study was carried out in unhospitalized dysthymic patients having a motor, ideational and cognitive inhibition and slowing.

These patients were divided into two parallel groups and treated under double-blind conditions for 8 weeks, either with sulbutiamine, or with a placebo, the treatments being allocated according to a randomization code.

We evaluated the effects of the treatment on:

1 - motor, verbal, ideational and cognitive slowing:

Widlocher scale of slowing, verbal chronometry, acoustic analysis of the speech.

2 - mood and anxiety:

MADRS scale (emotional dulling, decline in activity),

Abrams-Taylor scale,

Widlocher scale.

A net diminution of the motor, verbal and cognitive slowing in dysthymic patients treated with sulbutiamine was observed.

EXAMPLE 4
Effects of Sulbutiamine on Inhibition Symptoms of Major Depressive Patients Treated with a Tricyclic Antidepressant The study was carried out in patients hospitalized for a major depressive state and treated with clomipramine in a variable dose.

These patients were divided into 2 parallel groups and treated for 8 weeks, either with sulbutiamine, or with a placebo, the treatments being allocated according to a randomization code.

We evaluated the effects of the treatment on:

1 - motor, ideational and cognitive slowing:

Sheehan incapacity scale,

HARS scale (loss of interest, memory disorders),

MADRS scale (concentration disorders, decline in activity),

Widlocher scale,

Norris visual analog scale, self-evaluation of fatigue.

2 - mood and anxiety:

MADRS scale (affective dulling),

HARS scale,

Widlocher scale.

An improvement in the inhibition symptoms was observed in the group treated with sulbutiamine, in particular of the cognitive functions.

EXAMPLE 5
Effects of Sulbutiamine on Inhibition Symptoms of Deficient Schizophrenics Treated with a Neuroleptic The study was carried out on deficient schizophrenic patients treated as outpatients with a neuroleptic.

These patients were divided into two parallel groups, then treated under double-blind conditions for 12 weeks, either with sulbutiamine, or with a placebo, the treatments being allocated according to a randomization code.

The treatment was evaluated on:

1 - cognitive functions:

PANSS scale, trail making test,

Stroop test,

Norris visual analog scale,

MADRS scale (concentration disorders, decline in activity).

2 - executive functions:

Wisconsin card sorting test.

3 - mnesic functions:

Gröber and Buschke test.

4 - negative signs of schizophrenia:

PANSS scale.

5 - quality of life:

Heinrichs' quality of life scale.

A regression of the signs of schizophrenia was observed in the group treated with sulbutiamine, with an improvement in the quality of life in parallel.

We claim:

1. A method of treating Parkinson's Disease, schizophrenia, alcoholism, or dysthymia in a host in need thereof comprising administering to said host an effective amount of sulbutiamine.

2. The method of claim 1 wherein the sulbutiamine is administered in the form of a pharmaceutical composition containing one or more pharmaceutically acceptable vehicles.

* * * * *